United States Patent [19]

McCoy

[11] Patent Number: 4,501,915

[45] Date of Patent: * Feb. 26, 1985

[54] PREPARATION OF N-ALKYL-MONOSUBSTITUTED CARBAMATES

[75] Inventor: John J. McCoy, Media, Pa.

[73] Assignee: Atlantic Richfield Company, Los Angeles, Calif.

[ * ] Notice: The portion of the term of this patent subsequent to Aug. 9, 2000 has been disclaimed.

[21] Appl. No.: 173,515

[22] Filed: Jul. 30, 1980

[51] Int. Cl.³ .......................................... C07C 125/065
[52] U.S. Cl. .................................................. 560/157
[58] Field of Search ........................................ 560/157

[56] References Cited

U.S. PATENT DOCUMENTS

| | | | |
|---|---|---|---|
| 2,041,733 | 5/1936 | Werntz | 560/157 |
| 2,409,712 | 10/1946 | Schweitzer | 560/157 |
| 2,677,698 | 5/1954 | Deutschman | 560/157 |
| 2,806,051 | 9/1957 | Brockway | 560/157 |
| 2,871,259 | 1/1959 | Levy | 560/157 |

OTHER PUBLICATIONS

Roberts, "Basic Principles of Organic Chemistry", pp. 879–882, (1964).

*Primary Examiner*—Michael L. Shippen
*Attorney, Agent, or Firm*—Delbert E. McCaslin

[57] ABSTRACT

An improved process for the preparation of N-alkyl-monosubstituted carbamates by reacting an aliphatic primary amine, urea and a monohydric aliphatic alcohol in the presence of a strongly basic tertiary amine catalyst and optionally an inert solvent.

19 Claims, No Drawings

PREPARATION OF N-ALKYL-MONOSUBSTITUTED CARBAMATES

BACKGROUND OF THE INVENTION

U.S. Pat. No. 2,677,698 describes a process for the preparation of N-monosubstituted carbamic acid esters by reacting a primary amine with urea to prepare a 1,3-disubstituted urea which is separated from unreacted amine, urea and generated ammonia and then reacted in a second step with a mono-hydroxy alcohol to give the resultant N-monosubstituted carbamic acid ester.

U.S. Pat. No. 2,409,712 relates to the pyrolysis of N-alkyl carbamic alkyl esters discloses a method for the preparation of such carbamic esters by reacting urea, an amine such as laurylamine or beta (isobutoxymethoxy)ethylamine and alcohols such as ethoxyethoxyethanol to give the N-alkyl carbamic alkyl esters.

The carbamates of this invention may be employed in a number of commercial applications, for example, as insecticides, herbicides, medicinals and as chemical intermediates.

SUMMARY OF THE INVENTION

According to the present invention there is provided a much improved process for the preparation of N-alkyl-monosubstituted carbamic acid esters which comprises reacting an aliphatic primary amine, such as ethylamine, with urea and a monohydric aliphatic alcohol, such as ethanol, at a temperature of from about 125° C. to 250° C. in the presence of a strongly basic tertiary amine catalyst and optionally in the presence of an inert solvent.

It is a primary object of this invention therefore, to provide an improved process for the catalytic preparation of N-alkyl-substituted carbamates in high yield and high conversion of reactants.

It is another object of this invention to provide an improved reaction system for the conversion of an aliphatic primary amine, urea and an alcohol to N-alkyl-monosubstituted carbamic acid esters, such as ethyl-N-octyl-carbamate.

These and other objects and advantages of this invention will become apparent from the description of the invention which follows, and from the claims.

DETAILED DESCRIPTION OF THE INVENTION

In accordance with this invention an N-alkyl-monosubstituted carbamic acid ester is produced by reacting urea and a monohydric aliphatic alcohol having from 1 to 18 carbon atoms, with a primary aliphatic amine of the general formula $RNH_2$ wherein R is a straight or branched chain alkyl group containing from 1 to 18 carbon atoms, at a temperature in the range of from about 125° C. to 250° C. in the presence of a strongly basic tertiary amine as catalyst. Alternatively an inert solvent may be employed, although the reaction solvent may simply be the reactant alcohol employed in stoichiometric excess.

The reaction between the urea, alcohol and the aliphatic primary amine may be carried out in any suitable reactor, such as an autoclave, which is generally equipped with a means for agitation, means for regulating temperature and pressure and means for removing by-product ammonia, and possibly alcohol vapor. Although the order of addition of the reactants, solvents and catalyst components may vary, a general procedure for carrying out the reaction is to charge the urea, primary aliphatic amine, alcohol, inert solvent if used and a strongly basic tertiary amine catalyst into the reaction vessel and then heat the mixture to the desired temperature at atmospheric pressure or higher pressures, if required. The reaction can be carried out batchwise, semicontinuous, or as a continuous process. The reaction products are recovered and treated by any conventional method, such as distillation or fractionation to effect separation of the N-alkyl-monosubstituted carbamate from unreacted starting material, catalyst, solvent and by-products.

The aliphatic primary amines employed as reactants in the process of the present invention conform to the general formula $RNH_2$ wherein R is a straight or branched chain alkyl group containing from 1 to 18 carbon atoms. Representative aliphatic primary amines as hereinabove described include, for example, methylamine, ethylamine, n-propylamine, isopropylamine, n-, iso-, sec.-, and tert-butyl-amines, n-decylamine, n-dodecylamine, n-octylamine, n-tetradecylamine, allylamine, n-amylamine, and the like.

The alcohols which are employed in at least stoichiometric amounts based on the aliphatic primary amine employed in the reaction are the monohydric aliphatic alcohols containing from 1 to 18 carbon atoms. As indicated hereinabove, the alcohols may also act as the reaction solvent and in such application are generally employed in a molar excess based on the aliphatic primary amine employed to effect the reaction to produce the N-alkyl-monosubstituted carbamic acid esters. Representative alcohols which maybe employed in the process of this invention include, for example, methanol, ethanol, n-propanol, n- and iso-butyl alcohols, amyl alcohol, hexanol, heptanol, octanol, nonanol. decanol, n-dodecanol, n-pentadecanol, cetyl alcohol, stearyl alcohol, myristyl alcohol, 2-ethyl hexanol, 2-methyl pentanol, 2-ethyl-1-butanol, 3,5-dimethyl-1-hexanol, and the like. The lower aliphatic alcohols having 1 to 4 carbon atoms are preferred A general postulated equation for the reaction of the present invention may be represented as follows:

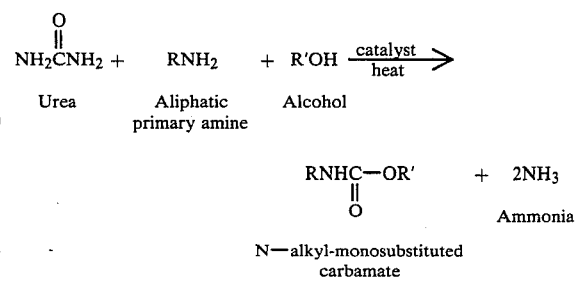

wherein R is as hereinabove described and R' represents the 1 to 18 carbon atom alkyl group of the monohydric aliphatic alcohol employed. A wide variety of N-alkyl-monosubstituted carbamates can be prepared by the process of this invention.

It has been discovered that greatly improved yields and increased reaction rates are obtained when the above reaction is carried out in the presence of strongly basic tertiary amine catalysts. In the absence of the tertiary amine catalyst the principal product is a disubstituted urea. The tertiary amine catalysts may be an aliphatic, cycloaliphatic, araliphatic or aromatic amine containing from 1 to 18 carbon atoms, which may be interrupted by oxygen, sulfur, nitrogen, sulfoxide or carbonyl substituents. In general, the tertiary amine employed as catalyst should be easily separated from reaction product and by-products. Representative amines suitable for use in the process of the invention include, for example, the trialkylamines such as the trimethyl, triethyl, tripropyl, tributyl, trihexyl, trioctyl, tridecyl, tridodecyl, etc. amines, triphenylamine, n-dodecyldimethylamine, n-tetradecyldimethylamine, n-hexyldecyldimethylamine, n-octyldecyldimethylamine, N,N,N',N'-tetramethylethylenediamine, 1,4-diazabicyclo[2.2.2]octane, 4(N,N-dimethylamino)pyridine, pyridine, 1,5-diazabicyclo[4.3.0]non-5-ene, 1,8-diazabicyclo[5.4.0]-undec-7-ene, methyldiethylamine, butyldimethylamine, benzyldimethylamine, and the like. The amount of tertiary amine catalyst which can be used in the process will generally range between about 0.1 to 200 mole percent, preferably 1 to 100 mole percent based on the aliphatic primary amine employed in the reaction, but greater or lesser quantities may be used if desired.

Although the process of the invention is preferably carried out using the monohydric aliphatic alcohol as the reaction solvent, as well as reactant, other solvents or mixtures of solvents which are stable and substantially chemically inert to the components of the reaction system may be employed as a co-solvent in the reaction system if desired. Suitable inert solvents which may be employed, and generally in amounts of from 0 to 50 weight percent based on the reaction mixture, include, for example, benzene, toluenes, xylenes, dichlorobenzene, tetrahydrofuran, 1,2-dimethoxylethane, diphenylether, nitrobenzene, diethyleneglycol dimethyl ether, triethyleneglycol dimethyl ether, dimethylsulfoxide, and the like.

The ratio of reactants may be varied over any convenient range. In general, the mole ratio of amine to urea may be between about 10:1 to 0.1:1 and is preferably between about 5:1 to 0.25:1. It is generally more convenient and preferred to employ the reactant alcohol as reaction solvent and thus in excess of the stoichiometric quantity required for the reaction. Amounts of up to 15 molar excess based on the amine employed may be conveniently employed. Greater amounts of alcohol may be employed but generally are not used due to the added burden of recovery.

The reaction of the present invention will proceed at temperatures of from about 125° C. to 250° C. It is generally preferred to operate the process at temperatures of from about 175° C. to 225° C. to obtain a convenient rate of reaction. The reaction temperature will depend on the particular N-alkyl-monosubstituted carbamic acid ester being produced and should be below the temperature at which significant decomposition of the product ester might occur.

The process of the present invention is generally carried out at atmospheric pressure or the autogenous pressure of the reaction system, although higher pressures of up to 50 atmospheres may be used and especially at the higher reaction temperatures or when the reaction temperature is above the boiling point of the alcohol and/or reactant amine. Subatmospheric pressure may be employed, if desired.

Ammonia resulting from the reaction must be removed during the course of the reaction, otherwise reduced yields of product carbamate are obtained. When the reaction is carried out at one atmosphere the ammonia is simply allowed to escape from the reaction vessel. In reactions where elevated pressures are employed provisions must be made to remove ammonia. A simple, convenient method is to strip the ammonia from the reactor with a dry inert gas, such as nitrogen and/or with the resulting alcohol vapor provided the alcohol employed is volatile at the reaction temperature. When the alcohol vapor is used to strip or aid in stripping the ammonia from the reactor, additional or makeup alcohol can be added to the reactor at a rate to compensate for the vapor loss.

The reaction time is generally dependent on the N-alkyl-monosubstituted carbamate being produced, the reaction temperature and the catalyst employed and will vary depending on whether the process is continuous or batch, but will generally range between about one to several hours.

The following examples are provided to illustrate the invention in accordance with the principles of this invention, but are not be construed as limiting the invention in any way except as indicated by the appended claims.

In the Examples which follow, the reactions were run in a 300 ml stainless steel stirred autoclave. The amine, urea and alcohol, along with the tertiary amine catalyst and co-solvent, if any, were charged to the reactor which was flushed with nitrogen and the reactor heated to the desired reaction temperature for a specified time period. During the reaction vaporized alcohol and product ammonia was stripped from the reactor. Makeup alcohol was pumped into the reactor at a rate closely approximating the alcohol removed. At the end of the reaction time, the autoclave was cooled to ambient temperature and the contents analyzed by liquid chromatography (LC) for conversion of amine and selectivities to N-alkyl-monosubstituted carbamates and by-products. The stripped alcohol collected in a dry ice trap was also analyzed for amine content. The amine conversions were calculated on the basis of moles of amine consumed by the reaction. Product selectivities were based on the moles of amine consumed in preparing the N-alkyl-monosubstituted carbamate and by-products.

EXAMPLE 1 (COMPARATIVE)

0.5 mol n-octylamine, 0.5 mol urea and 2.8 moles of dry ethanol (200 proof) was charged to the autoclave which was flushed several times with nitrogen and heated to 200° C. for a period of 3 hours. During the reaction period ethanol and by-product ammonia were stripped from the reactor with nitrogen at an average of 2.4 ml of ethanol per minute. The ethanol vapor containing ammonia and a small amount of n-octylamine was condensed in a dry ice cooled trap. Makeup ethanol was pumped into the autoclave at a rate closely approximating the amount stripped. After the reaction period, the autoclave was cooled and the contents, along with the ethanol condensate, analyzed. LC analysis showed an amine conversion of 100 percent. Selectivities to ethyl-N-octylcarbamate was 20 mole percent with 75 mole percent to di-n-octyl and other ureas.

EXAMPLES 2 TO 8

In Example 2 to 8, the general procedure as hereinabove described was repeated using various aliphatic amines, alcohols, tertiary amine catalysts and conditions with 0.5 mole of the urea reactant. The reaction conditions and results are set forth in the Table below showing mole percent conversion of amine with selectivities to product carbamate and by-product ureas.

| Example No. | Charge Moles | | | Conditions | | Amine Mole % Conversion | Mole % Selectivity to | | |
|---|---|---|---|---|---|---|---|---|---|
| | Amine (moles) | Alcohol (moles) | Catalyst (moles) | Temp °C. | Time Hours | | N—alkyl-Mono Substituted Carbamate | | By-Product Ureas* |
| 2 | n-octylamine (.5) | ethanol (2.8) | TEA[2] (.32) | 200 | 3 | 100 | EOC[6] | 80 | 15 |
| 3[1] | ethylamine (.5) | methanol (2.0) | DBU[3] (.01) | 175 | 3 | 100 | MEC[7] | 75 | 20 |
| 4 | n-dodecylamine (.5) | octanol (1.5) | pyridine (.12) | 150 | 2 | 100 | ODDC[8] | 32 | 58 |
| 5 | n-octylamine (.5) | decanol (1.8) | TEA (.40) | 200 | 3 | 100 | DOC[9] | 75 | 10 |
| 6 | n-octylamine (.5) | methanol (2.2) | DBN[4] (.05) | 200 | 3 | 100 | MOC[10] | 87 | 4 |
| 7 | n-dodecylamine (.5) | ethanol (3.0) | TEA (.50) | 175 | 3 | 100 | EDDC[11] | 60 | 30 |
| 8 | ethylamine (.5) | decanol (1.5) | TOA[5] (.02) | 150 | 3 | 100 | DEC[12] | 54 | 44 |

[1] 100 ml diglyme added as co-solvent
[2] TEA—triethylamine
[3] DBU—1,8-Diazabicyclo[5.4.0]undec-7-ene
[4] DBN—1,5-Diazabicyclo[4.3.0]non-5-ene
[5] TOA—trioctylamine
[6] EOC—ethyl-N—octylcarbamate
[7] MEC—methyl-N—ethylcarbamate
[8] ODDC—octyl-N—dodecylcarbamate
[9] DOC—decyl-N—octylcarbamate
[10] MOC—methyl-N—octylcarbamate
[11] EDDC—ethyl-N—dodecylcarbmate
[12] DEC—decyl-N—ethylcarbamate
*Includes by-product ureas such as dialkylureas, alkyl ureas, etc.

I claim:

1. A process for the preparation of an alkyl-N-monosubstituted carbamic acid ester which comprises reacting an aliphatic primary amine having the formula $RNH_2$ wherein R is a straight or branched chain alkyl group containing from 1 to 18 carbon atoms, with urea and at least a stoichiometric amount of a monohydric aliphatic alcohol, based on the aliphatic amine and, having from 1 to 18 carbon atoms at a temperature in the range of from about 125° C. to 250° C. in the presence of a catalytic amount of a tertiary amine containing from 1 to 18 carbon atoms and selected from the group consisting of trialkylamines wherein the alkyl groups are the same, triphenylamine, n-dodecyldimethylamine, n-tetradecyldimethylamine, n-hexyldecyldimethylamine, n-octyldecyldimethylamine, N,N,N',N'-tetramethylethylenediamine, 1,4-diazabicyclo[2.2.2]octane, 4(N,N-dimethylamino)pyridine, pyridine, 1,5-diazabicyclo[4.3.0]non-5-ene, 1,8-diazabicyclo[5.4.0]undec-7-ene; methyldiethylamine, butyldimethylamine and benzyldimethylamine.

2. A process according to claim 1 wherein the aliphatic primary amine is selected from the group consisting of ethylamine, n-octylamine and n-dodecylamine.

3. A process according to claim 2 wherein the aliphatic primary amine is n-octylamine.

4. A process according to claim 1 wherein the molar ratio of aliphatic primary amine to urea employed in the reaction is between about 10:1 to 0.1:1.

5. A process according to claim 4 wherein the molar ratio is between 5:1 to 0.25:1.

6. A process according to claim 1 wherein the monohydric aliphatic alcohol is selected from the group consisting of methanol, ethanol, decanol, and n-octanol.

7. A process according to claim 6 wherein the alcohol is methanol.

8. A process according to claim 6 wherein the alcohol is ethanol.

9. A process according to claim 1 wherein the alcohol is employed at a molar ratio of from about 1:1 to 15:1 based on the aliphatic primary amine.

10. A process according to claim 1 wherein the tertiary amine catalyst is employed in an amount of from about 0.1 to 200 mole percent based on the aliphatic primary amine employed.

11. A process according to claim 10 wherein the tertiary amine is employed in an amount of from 1 to 100 mole percent.

12. A process according to claim 1 wherein the tertiary amine catalyst is selected from the group consisting of triethylamine, trioctylamine, and pyridine.

13. A process according to claim 12 wherein the tertiary amine catalyst is triethylamine.

14. A process according to claim 12 wherein the tertiary amine catalyst is pyridine.

15. A process according to claim 1 wherein the catalyst is 1,8-diazabicyclo[5.4.0]undec-7-ene.

16. A process according to claim 1 wherein the catalyst is 1,5-diazabicyclo[4.3.0]non-5-ene.

17. A process according to claim 1 wherein the reaction temperature is in the range of from about 175° C. to 225° C.

18. A process according to claim 1 wherein the reaction is carried out under a pressure of from 1 to 50 atmospheres.

19. A process according to claim 1 wherein the reaction is carried out in the presence of an inert solvent.

* * * * *